United States Patent [19]
Simon et al.

[11] Patent Number: 5,939,084
[45] Date of Patent: Aug. 17, 1999

[54] AQUEOUS PHASE DERMATOLOGICAL/ COSMETIC COMPOSITIONS COMPRISING SOLUBILIZED MELATONIN VALUES

[75] Inventors: Pascal Simon, Vitry Sur Seine; Dominique Bordeaux, Saint Michel Sur Orge, both of France; Didier Gagnebien, Westfield, N.J.

[73] Assignee: Societe L'Oreal S.A., Paris, France

[21] Appl. No.: 08/942,395

[22] Filed: Oct. 10, 1997

[30] Foreign Application Priority Data

Oct. 10, 1996 [FR] France ................... 96 12387

[51] Int. Cl.⁶ ............... A61K 7/00; A61K 9/16; A61K 31/40; A61K 31/405
[52] U.S. Cl. ............ 424/401; 424/490; 514/408; 514/415; 514/419; 514/844; 514/873; 514/937; 514/944; 514/945
[58] Field of Search ............... 424/401, 490; 514/408, 415, 419, 844, 873, 937, 944, 945

[56] References Cited

FOREIGN PATENT DOCUMENTS

| | | |
|---|---|---|
| 0438856 | 7/1991 | European Pat. Off. . |
| 0578620 | 1/1994 | European Pat. Off. . |
| 0 578 620 | 12/1994 | European Pat. Off. . |
| 61-221104 | 10/1986 | Japan . |
| 86/05093 | 9/1986 | WIPO . |

OTHER PUBLICATIONS

Database WPI, Week 8646, Derwent Publications Ltd., London, GB; AN 86–300704 XP002032177: "Cosmetic compsn. used to protect skin—comprises melatonin in soln. cream, etc." . . . Oct. 1, 1986.

Database WPI, Week 9304, Derwent Publications Ltd., London, GB; AN 93–033597 XP002032178: "Cosmetic compsn. used to protect skin—comprises melatonin in soln. cream, etc." . . . Oct. 1, 1986.

Database WPI, Week 8644, Derwent Publications Ltd., London, GB; AN 86–289026 XP002032179: "Hair tonic compsn.—contg. melatonin for reduced toxicity" . . . Sep. 20, 1986.

*Primary Examiner*—Shelley A. Dodson
*Assistant Examiner*—Marina Lamm
*Attorney, Agent, or Firm*—Burns, Doane, Swecker & Mathis, L.L.P.

[57] ABSTRACT

Stable, recrystallization-resistant dermatological/cosmetic compositions, well suited for preventing/treating oxidative stress of the skin, comprise a substantially ethanol-free aqueous phase, the aqueous phase containing an active amount of solubilized melatonin values and an amount of at least one glycol effective to dissolve such melatonin values.

18 Claims, No Drawings

AQUEOUS PHASE DERMATOLOGICAL/COSMETIC COMPOSITIONS COMPRISING SOLUBILIZED MELATONIN VALUES

BACKGROUND OF THE INVENTION

1. Technical Field of the Invention

The present invention relates to the formulation of glycols into cosmetic compositions comprising a substantially alcohol-free aqueous phase, to solubilize therein effective amounts of melatonin or analog thereof.

The present invention also relates to novel alcohol-free aqueous cosmetic compositions comprising melatonin or analog thereof and a solubilizing amount of at least one glycol.

2. Description of the Prior Art

Melatonin, or N-acetyl-5-methoxytryptamine, known especially for its bioactivity on the circadian rhythm regulating hormone production, is also known for its antioxidizing activity (Reiter R. J., *Verhandung der Deutschen Zoologischen Gesellschaft*, 87 (2), 195–204 (1994); Reiter R. J. et al., *Neuroendocrinol Letter*, 15 (1-3), 103–113 (1993); Reiter R. J. et al., *J. Pineal Res.*, 18 (1), 1–11 (1995), in particular its antiradical activity (Reiter R. J. et al., *Brazilian Journal of Medical and Biological Research*, 26 (22), 1141–1155 (1993)). The majority of studies on the antioxidant properties of melatonin are concerned with oxidation phenomena related to aging of the brain (Pooggeler B. et al., *J. Pineal Res.*, 14 (4), 151–168 (1993); Cagnoli C. M. et al., *J. Pineal Res.*, 18 (4), 222–226 (1995); Melchiorri D. et al., *FASEB J.*, 9 (12), 1205–1210 (1995); Sewerynek E. et al., *Neuroscience Letters*, 195 (3), 203–205 (1995)).

Melatonin has also been described for formulation into dermocosmetics for improving the appearance of skin (JP-61/221,104; WO-86/05,093) or for protecting the skin against the deleterious effects of UV radiation (EP-0,438,856; E. Bangha et al., *Dermatology*, 191, [2], 176 (1995)). It is recommended to employ melatonin at concentrations of between $10^{-4}\%$ and 10% by weight with respect to the total weight of the composition.

Thus, WO-86/05,093 describes a cosmetic composition comprising melatonin for increasing the sensitivity of the skin to estrogens, in particular for the treatment of acne or the prevention of hair loss. The amounts of melatonin recommended in this application are generally between $10^{-4}$ and more than 1% by weight with respect to the total weight of the composition.

Similarly, EP-438,856, relating to compositions for protecting the skin against the damaging effects of UV radiation, recommends amounts of melatonin of between 1% and 10% by weight for topical compositions, the only example of this type of composition being an anhydrous ointment comprising 10% of melatonin.

In order for melatonin applied topically to have satisfactory effectiveness, it is essential that it be well dissolved in the vehicle therefor. It has been determined that melatonin, at the doses heretofore recommended, is soluble neither in water nor in the oils formulated into cosmetics. Thus, melatonin is insoluble at 1% by weight in water, mineral oils (liquid petrolatum), fatty esters (2-ethylhexyl palmitate, dodecyl benzoate, 2-octyldodecyl neopentanoate), fatty alcohol ethers (polyoxypropylenated myristyl alcohol, polyoxypropylenated stearyl alcohol, 2-ethylhexyl glyceryl ether palmitate) or fatty alcohols (octyldodecanol, isostearyl alcohol, 2-hexyl-1-decyl alcohol).

To properly dissolve melatonin or analogs thereof in fluid compositions, such as creams, gels or lotions, it is necessary to include ethanol.

Thus, WO-86/05,093 recommends employing between 10% and 30% by weight of ethanol.

Likewise, JP-61/221,104 describes different solutions comprising between $10^{-4}\%$ and 0.01% by weight of melatonin and between 3% and 8% by weight of ethanol, the melatonin/ethanol ratio by weight being between 1/30,000 and 1/500.

Too, EP-578,620 describes different compositions in the form of gels comprising between 5% and 30% of ethanol, the melatonin/alcohol ratio being between 1/450 and 1/10.

Indeed, for compositions as described in WO-86/05,093, it is necessary to incorporate more than 35% by weight of ethanol in order to obtain a stable recrystallization-free composition containing 0.5% by weight of melatonin. The greater the amount of melatonin or analog thereof in the composition, the greater the amount of alcohol required to provide a stable composition.

Including such amounts of alcohol is inappropriate for the formulation of cosmetic compositions, since alcohols cause drying of the skin and the phenomena of irritation, warming and red blotches. While such phenomena may be accepted for pharmaceutical compositions, where a balance is sought between the beneficial effect of the active agent or principle (in this case melatonin) and its side effects and/or those of the composition, this is not the case for cosmetic compositions, which have to be free of any undesirable side effect unacceptable to the user.

SUMMARY OF THE INVENTION

It has now unexpectedly been determined that glycols permit the dissolution of melatonin or analog thereof in substantially ethanol-free aqueous compositions, an option heretofore never considered.

Briefly, the present invention thus features formulating effective amounts of at least one glycol to dissolve or solubilize melatonin or analog thereof in compositions comprising a substantially ethanol-free aqueous phase.

DETAILED DESCRIPTION OF BEST MODE AND SPECIFIC/PREFERRED EMBODIMENTS OF THE INVENTION

More particularly according to the present invention, by "effective amount" of at least one glycol is intended an amount sufficient to enable melatonin or analog thereof to be dissolved in the aqueous phase of the composition and to enable a stable composition to be obtained, without recrystallization of the melatonin or analog thereof.

By "stable composition" is preferably intended a composition in which melatonin or analog thereof does not crystallize when it is permitted to stand for at least 4 weeks at 4° C.

Of course, the amount of glycol effective for dissolving melatonin or analog thereof will depend on the amount of melatonin or analog thereof included in the composition.

This amount will also depend on the water content of the composition comprising melatonin or analog thereof.

Advantageously, the ratio by weight of melatonin to glycol effective for dissolving melatonin or analog thereof ranges up to 1/5. It will be appreciated that the lower limit of this ratio will depend on the glycol employed, on its harmlessness or inertness and on the absence of side effects of irritation or of red blotches when they are applied at excessively high doses.

In the case of a purely aqueous composition, namely, substantially free of fatty phase, such as an aqueous gel or lotion, the melatonin/glycol ratio by weight preferably ranges from 1/60 to 1/15.

In the case of a composition also comprising a fatty phase, such as an emulsion of oil-in-water (O/W) or water-in-oil (W/O) type, the melatonin/glycol ratio by weight preferably ranges from 1/15 to 1/5.

By "substantially ethanol-free composition" is intended a composition which does not comprise ethanol or which comprises trace amounts of ethanol, amounts insufficient to dissolve or to improve the solubility of melatonin. A substantially ethanol-free composition preferably does not comprise any ethanol.

The glycols according to the invention are advantageously selected from among saturated or unsaturated, linear or branched, $C_3$–$C_{10}$ hydrocarbons comprising at least two free hydroxyl functional groups, polyalkylene glycols comprising at least 2 alkylene units, and polyalkylene glycol ethers.

By "linear or branched $C_3$–$C_{10}$ hydrocarbons comprising at least two free hydroxyl functional groups" are preferably intended hydrocarbons comprising a primary hydroxyl functional group and at least one second hydroxyl functional group in the β-position with respect to the first. Particularly preferred are saturated or unsaturated, linear or branched, $C_3$–$C_{10}$ alkylene glycols, such as propylene glycol or 1,3-butylene glycol.

When the hydrocarbon is unsaturated, it can comprise one, two or more sites of unsaturation, such as isoprene glycol.

By "alkylene" are preferably intended saturated or unsaturated, linear or branched, $C_2$–$C_4$ alkylene moieties. Particularly preferred are polyethylene glycols comprising 6 to 40 ethylene glycol structural units and dipropylene glycol.

By "polyalkylene glycol ether" are preferably intended linear or branched $C_1$–$C_4$ monoalkyl ethers of the polyalkylene glycols described above, for example diethylene glycol monoethyl ether (transcutol).

Exemplary melatonin analogs according to the present invention include such derivatives as 5-methoxytryptamine, 5-methoxytryptophan, 5-methoxytryptophol, 5-methoxyindole-3-acetic acid and 6-hydroxymelatonin. Also exemplary are the melantoninergic agonists described in WO-95/17,405, EP-0,447,285, EP-0,527,687, EP-0,530,087 and EP-0,591,057. These compounds are natural or synthetic in origin.

The subject compositions can include high contents of melatonin or analog thereof, up to 10% by weight with respect to the total weight of the composition. The present invention is particularly well suited for the formulation of compositions comprising from $10^{-4}$% to 10% by weight of melatonin or analog thereof, preferably from 0.1% to 5% by weight. Of course, the present invention also features compositions comprising less than $10^{-4}$% by weight of melatonin or analog thereof, but requiring inclusion of an appropriate polyol in order to ensure its solubility in the aqueous phase.

The present invention also features substantially ethanol-free topically applicable compositions comprising melatonin or analog thereof in an aqueous phase and an effective amount of at least one glycol to dissolve said melatonin or analog thereof, and wherein the melatonin/glycol ratio by weight ranges from 1/60 to 1/5.

The dermocosmetic compositions according to the invention advantageously have a viscosity ranging from 0.5 to 8 Pa.s.

The topical compositions into which melatonin or analog thereof is formulated comprise a cosmetic or dermatological composition and can be provided in all conventional pharmaceutical dosage forms for topical application and the physiologically acceptable vehicle, diluent or carrier therefor can be any standard vehicle or medium for a cosmetic or dermatological composition. The subject compositions can be formulated as an aqueous solution, or an oily suspension, or a dispersion of the lotion or serum type, or as an emulsion having a liquid or semi-liquid consistency of the milk type, obtained by dispersion of a fatty phase into an aqueous phase (O/W) or vice-versa (W/O), or as a suspension or emulsion having a soft consistency of the aqueous gel or cream type, or as microcapsules or microparticles, or as vesicular dispersions of ionic and/or non-ionic type. These compositions are formulated according to the usual techniques.

The amounts of the different constituents of the compositions are those conventionally employed in the fields under consideration.

The subject compositions constitute, in particular, cleansing, protection, treatment or care creams for the face, for the hands, for the major anatomical folds or for the body (for example day creams, night creams, makeup removal creams, foundation creams or antisun or sunscreen creams), fluid foundations, makeup removal milks, protection or care body milks, antisun or sunscreen milks, or lotions, gels or foams for caring for the skin, such as cleansing lotions, antisun lotions, artificial tanning lotions, and the like.

When the composition is an emulsion, the proportion of the fatty phase can range from 5% to 80% by weight and preferably from 5% to 50% by weight with respect to the total weight of the composition. The oils, waxes, emulsifiers and coemulsifiers formulated into the composition in the emulsion form are those conventional in the cosmetics field. The emulsifier and the coemulsifier are advantageously present in such compositions in a proportion ranging from 0.3% to 30% by weight and preferably from 0.5% to 20% by weight with respect to the total weight of the composition. The emulsion can, in addition, contain lipid vesicles.

The subject cosmetic or dermatological compositions can also contain adjuvants and additives usual in the cosmetics or dermatological field, such as hydrophilic or lipophilic gelling agents, hydrophilic or lipophilic additives, preservatives, antioxidants, solvents, fragrances, fillers, screening agents, odor absorbers and colorants. The amounts of these different adjuvants and additives are those conventional in these fields and, for example, range from 0.01% to 10% of the total weight of the composition. These adjuvants and additives, depending on their nature, can be introduced into the fatty phase, into the aqueous phase and/or into lipid spherules.

Exemplary oils and waxes include mineral oils (liquid petrolatum), vegetable oils (liquid fraction of karite butter, sunflower oil), animal oils (perhydrosqualene), synthetic oils (Purcellin oil), silicone oils or waxes (cyclomethicone) and fluorinated oils (perfluoropolyethers), beeswax or carnauba or paraffin wax. Fatty alcohols and fatty acids (stearic acid) can be added to these oils.

Exemplary emulsifiers include, for example, glycerol stearate, polysorbate 60 and the PEG-6/PEG-32/glycol stearate mixture marketed under the trademark Tefose® 63 by Gattefosse.

Exemplary hydrophilic gelling agents according to the invention include the carboxyvinyl polymers (carbomer), acrylic copolymers, such as acrylate/alkyl acrylate copolymers, polyacrylamides, polysaccharides, such as hydroxypropylcellulose, natural gums and clays, and exemplary lipophilic gelling agents include the modified clays, such as bentones, or metal salts of fatty acids, such as aluminum stearates.

Insofar as they do not interfere or interact with the activity of the melatonin, the compositions of the present invention can contain other active ingredients suitable, in particular, for the prevention and/or for the treatment of skin conditions/afflictions.

The compositions according to the invention are particularly well suited for preventing or treating oxidative stress of the skin and/or of its adnexa, in particular related to UV irradiation, to aging, to inflammation, to alopecia, and the like.

In order to further illustrate the present invention and the advantages thereof, the following specific examples are given, it being understood that same are intended only as illustrative and in nowise limitative.

In said examples to follow, all parts and percentages are given by weight with respect to the total weight of the composition.

EXAMPLE 1

Study of the stability of the subject compositions:

The stability of melatonin in different compositions was studied:

(a) Stability in an aqueous/alcoholic solution:

The stability of an aqueous/alcoholic solution containing 0.5% of melatonin was studied at 4° C. for different concentrations of ethanol. The results obtained are reported in Table I below.

TABLE I

| Ethanol % | 20% | 30% | 35% | 40% |
|---|---|---|---|---|
| Stability after 4 weeks | no | no | yes | yes |
| Stability after 8 weeks | no | no | no | yes |

At least 35% of ethanol was thus required in order to provide a stable composition containing 0.5% of melatonin.

(b) Stability in an aqueous/glycolic composition:

The stability of an aqueous/glycolic solution containing 0.5% of melatonin was studied at 4° C. for different concentrations of isoprene glycol. The results obtained are reported in Table II below.

TABLE II

| Isoprene glycol % | 20% | 30% | 50% |
|---|---|---|---|
| Stability after 4 weeks | yes | yes | yes |
| Stability after 8 weeks | yes | yes | yes |

The isoprene glycol made it possible to provide compositions containing 0.5% by weight of melatonin which were stable up to 8 weeks at 4° C., for glycol concentrations of 20% in water.

Similarly, isoprene glycol, butylene glycol, dipropylene glycol or polyethylene glycol-6 made it possible to obtain compositions containing 2% by weight of melatonin which were stable up to 8 weeks at 4° C., at glycol concentrations of 50% in water.

Under similar conditions, dipropylene glycol or polyethylene glycol-6 provided compositions containing 5% by weight of melatonin which were stable up to 8 weeks at 4° C., at glycol concentrations of 50% in water.

EXAMPLE 2

Compositions According to the Invention:

The compositions (a) to (d) below were formulated according to usual techniques. They were stable for at least 4 weeks at 4° C. Melatonin was compatible with the excipient.

(a) Lotion:

| | |
|---|---|
| Butylene glycol | 20.00% |
| Propylene glycol | 15.00% |
| Citric acid | 0.02% |
| Sodium citrate | 0.05% |
| Melatonin | 2.00% |
| Fragrance | 0.05% |
| Preservative | 0.10% |
| Water | q.s. for 100 |

This composition was stable. No crystallization was observed after 4 weeks at 4° C.

(b) Aqueous Gel:

| | |
|---|---|
| Isoprene glycol | 20.00% |
| Glycerol | 5.00% |
| Acrylate/$C_{10}$–$C_{30}$ alkyl acrylate crosslinked copolymer (Pemulen TR2, marketed by Goodrich) | 0.50% |
| Phenylethyl alcohol | 0.50% |
| Melatonin | 0.50% |
| Diazolidinylurea | 0.10% |
| Water | q.s. for 100 |

This composition was stable. No crystallization was observed after 4 weeks at 4° C.

(c) W/O Emulsion:

| | |
|---|---|
| Diglyceryl diisostearate | 2.00% |
| Laurylmethicone copolyol (Dow Corning Q-2-5200) | 2.00% |
| Liquid petrolatum | 10.00% |
| Cyclomethicone | 15.00% |
| PEG-4 | 15.00% |
| Butylene glycol | 20.00% |
| Melatonin | 4.00% |
| Magnesium sulfate | 1.00% |
| Methylparaben | 0.25% |
| Chlorphenesin | 0.30% |
| Water | q.s. for 100 |

This composition was also stable. No crystallization was observed after 4 weeks at 4° C.

(d) O/W Emulsion:

| | |
|---|---|
| Glyceryl stearate | 1.00% |
| Glyceryl stearate PEG 100 | 2.00% |
| Behenyl alcohol | 2.50% |
| Stearic acid | 1.50% |
| Beeswax | 4.00% |
| Capric/caprylic triglyceride | 7.00% |
| Hydrogenated polyisobutene (Parleam) | 12.00% |
| Polyacrylamide/$C_{13-14}$ isoparaffin/laureth-7 (Sepigel 305, marketed by Seppic) | 0.05% |
| Isoprene glycol | 20.00% |
| Melatonin | 3.00% |
| Chlorphenesin | 0.30% |
| Methylparaben | 0.20% |
| Water | q.s. for 100 |

This composition was also stable. No crystallization was observed after 4 weeks at 4° C.

EXAMPLE 3 (Comparative)

The O/W emulsion described at page 7, lines 5 to 20 of EP-578,620 was reproduced. In this composition, containing 0.08% by weight of melatonin, the melatonin/glycol ratio was 1/100. No solubilization of the melatonin was observed. It remained crystalline in the emulsion.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable, recrystallization-resistant dermatological/cosmetic composition which comprises a substantially ethanol-free aqueous phase, said aqueous phase comprising an active amount of solubilized melatonin or analog thereof and an amount of at least one glycol effective to dissolve said melatonin or analog thereof, wherein said at least one glycol comprises a saturated or unsaturated, linear or branched, $C_3$–$C_{10}$ hydrocarbon having at least two free hydroxyl functional groups, or a linear or branched $C_1$–$C_4$ monoalkyl ether of a polyalkylene glycol.

2. The dermatological/cosmetic composition as defined by claim 1, wherein the melatonin or analog thereof/glycol ratio by weight is less than or equal to 1/5.

3. The dermatological/cosmetic composition as defined by claim 1, substantially free of fatty phase.

4. The dermatological/cosmetic composition as defined by claim 3, wherein the melatonin or analog thereof/glycol ratio by weight ranges from 1/60 to 1/15.

5. The dermatological/cosmetic composition as defined by claim 1, further comprising a fatty phase.

6. The dermatological/cosmetic composition as defined by claim 5, wherein the melatonin or analog thereof/glycol ratio by weight ranges from 1/15 to 1/5.

7. The dermatological/cosmetic composition as defined by claim 1, wherein said at least one glycol is a hydrocarbon having a primary hydroxyl functional group and at least one second hydroxyl functional group in the β-position with respect to the first.

8. The dermatological/cosmetic composition as defined by claim 7, wherein said at least one glycol comprising a saturated or unsaturated, linear or branched, $C_3$–$C_{10}$ alkylene glycol.

9. The dermatological/cosmetic composition as defined by claim 8, wherein said at least one glycol is selected from the group consisting of propylene glycol, 1,3-butylene glycol and a isoprene glycol.

10. The dermatological/cosmetic composition as defined by claim 1, comprising no greater than 10% by weight of said solubilized melatonin or analog thereof.

11. The dermatological/cosmetic composition as defined by claim 10, comprising from $10^{-4}$% to 10% by weight of said solubilized melatonin or analog thereof.

12. The dermatological/cosmetic composition as defined by claim 11, comprising from 0.1% to 5% by weight of said solubilized melatonin or analog thereof.

13. The dermatological/cosmetic composition as defined by claim 1, wherein said melatonin or analog thereof is N-acetyl-5-methoxytryptamine.

14. The dermatological/cosmetic composition as defined by claim 1, wherein said melatonin or analog thereof is selected from the group consisting of 5-methoxytryptamine, 5-methoxytryptophan, 5-methoxytryptophol, 5-methoxyindole-3-acetic acid, 6-hydroxymelatonin, and a melatoninergic agonist.

15. The dermatological/cosmetic composition as defined by claim 1, in the form of an aqueous solution, oily suspension, dispersion, emulsion, milk, gel, cream, lotion, foam, microcapsules, or microparticles.

16. The dermatological/cosmetic composition as defined by claim 1, having a viscosity ranging from 0.5 to 8 Pa.s.

17. A method for eliciting an active melatonin effect on the skin of an individual in need of such treatment, comprising topically applying thereto an effective amount of the dermatological/cosmetic composition as defined by claim 1.

18. The method as defined by claim 17, for preventing or treating oxidative stress of the skin.

* * * * *